United States Patent [19]

Payne et al.

[11] 4,173,586
[45] Nov. 6, 1979

[54] PROCESS FOR CLEAVAGE OF UNSATURATED MULTI-CYCLIC KETONES

[75] Inventors: Larry W. Payne, Clute; Howard E. Miller; James R. Ryffel, both of Lake Jackson, all of Tex.

[73] Assignee: Badische Corporation, Williamsburg, Va.

[21] Appl. No.: 942,845

[22] Filed: Sep. 15, 1978

[51] Int. Cl.$^2$ .......................... C07C 27/00; C07C 3/30
[52] U.S. Cl. ................................ 260/586 R; 568/835; 585/353; 585/357
[58] Field of Search ...................... 260/586 R, 666 A; 568/835

[56] References Cited

U.S. PATENT DOCUMENTS 3,574,757   4/1971   Collier ............................. 260/586 R

FOREIGN PATENT DOCUMENTS

| 253194 | 3/1963 | Australia | 260/586 R |
|---|---|---|---|
| 683377 | 3/1964 | Canada | 260/586 R |
| 95459 | 6/1960 | Czechoslovakia . | |
| 93948 | 7/1962 | Denmark | 260/586 R |
| 932966 | 9/1955 | Fed. Rep. of Germany | 260/586 R |
| 1007772 | 5/1957 | Fed. Rep. of Germany . | |
| 1283076 | 3/1961 | France | 260/586 R |
| 38-07730 | 6/1963 | Japan | 260/586 R |
| 39-26965 | 11/1964 | Japan . | |
| 111121 | 11/1961 | Pakistan | 260/586 R |
| 918407 | 2/1963 | United Kingdom | 260/586 R |

OTHER PUBLICATIONS

Freidlin et al, "Izvest. Akao. Nauk, SSSR, Otdel. Khim. Nauk.", 1957, pp. 512–514, (C.A. 51:15422f (1957)).
Richter et al., "Chem prumysl", 8, pp. 62–64, (1958), (C.A. 52:15444f, 1957).

Primary Examiner—Norman Morganstern
Attorney, Agent, or Firm—George F. Helfrich

[57] ABSTRACT

A process for cleavage of unsaturated multi-cyclic ketones involves thermal cracking of the liquid ketone at elevated temperatures in the absence of water to produce cyclohexanone and a variety of other cleavage products. Para-toluenesulfonic acid and transition metal oxides are advantageously employed as catalysts.

5 Claims, No Drawings

PROCESS FOR CLEAVAGE OF UNSATURATED MULTI-CYCLIC KETONES

BACKGROUND OF THE INVENTION

1. Field of the Invention

This invention relates generally to the preparation of cyclic organic compounds. In particular it relates to the thermal cleavage of unsaturated multi-cyclic ketones to produce cyclohexanone and other cleavage products including cyclohexene and cyclohexanol.

2. Prior Art Statement

References considered of particular pertinence are set forth below.

a. U.S. Pat. No. 3,574,757 (Collier) describes a process for hydrolytic cleavage of unsaturated bicyclic ketones which involves contacting a substantially anhydrous ketone with superheated steam and caustic. Although the starting material in this case is free of water, steam is added to the reaction mixture; part of this steam is consumed in the reaction which produces cyclohexanone. By way of contrast, the process of our invention uses no water whatsoever, and is thus a thermal rather than a hydrolytic cleavage. The hydrolytic cleavage of, for example, 2-(1-cyclohexenyl)cyclohexanone or 2-cyclohexylidenecyclohexanone proceeds in a manner such that one molecule of water reacts with one molecule of bicyclic ketone to yield two molecules of cyclohexanone. Surprisingly, it has now been found that cyclohexanone as well as other compounds are obtained when a thermal cleavage reaction in the absence of water is carried out according to the process of our invention. As in the hydrolytic cleavage reaction, the thermal cleavage reaction proceeds readily when the starting material is an essentially pure bicyclic ketone, or a mixture containing said bicyclic ketones such as the high boiling fraction obtained from the distillation of cyclohexanone and cyclohexanol. It is known that said high-boiling fractions contain a variety of multi-cyclic compounds such as 2-(1-cyclohexenyl)cyclohexanone, 2-cyclohexylidenecyclohexanone, and various other mutli-cyclic oxygenated compounds arising as condensation products of cyclohexanone or cyclohexanol. Thus, the chemical reaction of our process is different from that of U.S. Pat. No. 3,574,757, even though some operating conditions may be somewhat similar. Other references such as German patent Nos. 927,688 and 946,443, and Czech patent No. 95,459 describe variations of the hydrolytic cleavage process.

b. Japanese Pat. No. 39-26965 describes a process for heat-treating of a mixture of multi-cyclic compounds containing unsaturated bicyclic ketones which involves heating the mixture in the presence of water and an inorganic acid catalyst at atmospheric pressure, and recovering cyclohexanone and cyclohexene from a portion of the mixture. By way of contrast, the process of our invention requires no water whatsoever and may be carried out without the use of a catalyst. Furthermore, it has been found that the addition of small amounts of water as low as three to four percent by weight of the starting material such as used in the examples of this reference gives significantly different results compared to conducting the cleavage reaction using a substantially dry starting material containing less than about one percent of water. Surprisingly, the cleavage reaction does not cease in the absence of water, but shifts from hydrolytic to thermal along with a corresponding shift in the amounts and percentages of cleavage products, especially cyclohexanone.

Thus, the cited references do not, whether alone or in combination, teach, suggest, or make obvious our invention, since the reactions therein are concerned with hydrolytic cleavage rather than thermal cleavage as in our process. Furthermore, the referenced art does not lead a person of ordinary skill in the art to predict with any degree of certainty the consequences of not having water present; experimental effort is essential.

SUMMARY OF THE INVENTION

A primary object of the present invention is to provide an economical, yet efficient and efficacious process for the cleavage of multi-cyclic ketones, thereby obviating disadvantages inherent in processes of the prior art.

This object is achieved by the provision of a process which comprises confining a substantially dry unsaturated multi-cyclic ketone at a temperature from about 150° to 350° C. under a pressure high enough to ensure that a liquid phase is present, and recovering the products therefrom by conventional distillation methods well known to those with skill in the art. For the purposes of this disclosure, the phrase "substantially dry" includes material containing up to about one percent by weight of water based on the weight of the multi-cyclic ketone or mixture thereof. The multi-cyclic ketone is advantageously employed as a component of a high-boiling fraction from the distillation of cyclohexanone and cyclohexanol. Especially beneficial results are obtained in the practice of the present invention if a bicyclic ketone, or mixture thereof (e.g., the high boiling fraction from the distillation of cyclohexanone and cyclohexanol, supra) is confined substantially at or above the vapor pressure of the bicyclic ketone or mixture thereof, respectively.

Outstanding results are obtained in the practice of the present invention if para-toluenesulfonic acid is employed as a catalyst for the cleavage reaction.

Outstanding results are also obtained in the practice of the present invention if a catalyst is employed in the form of (a) nickel oxide/molybdenum oxide on an inert support, or (b) cobalt oxide/molybdenum oxide on an inert support, or (c) a mixture comprising (a) and (b) in various proportions.

DESCRIPTION OF THE PREFERRED EMBODIMENTS

For a more complete understanding of the present invention, including its primary object and benefits, reference should be made to the description of the preferred embodiments thereof, which is set forth in detail below. All percentages in the following examples are on a weight basis.

EXAMPLE 1

In each of a series of experimental runs, a liquid residue from the distillation of cyclohexanone and cyclohexanol having from about 10-40 percent by weight of 2-(1-cyclohexenyl)cyclohexanone and 2-cyclohexylidenecyclohexanone was placed in a completely sealed stainless steel reaction bomb and heated at a temperature between 150° and 350° C. for a period of ½ to 6 hours. Each bomb was then rapidly cooled. No raw materials other than the liquid residue were required.

Temperatures of 200°–350° C. and reaction times from 1 to 3 hours are preferred ranges. Below a temperature of about 200° C. and without a catalyst, the thermal cleavage reaction proceeds so slowly as to be impractical. Above about 350° C., other thermal cleavage and pyrolysis reactions may begin to take place giving undesirable products. Within the stated range of temperature, the process of our invention proceeds readily and yields the stated products with a minimum of side reactions when the starting material is the high boiling fraction from the distillation of cyclohexanone and cyclohexanol. As should be readily apparent to those with skill in the art of chemical reactions, the reaction time is strongly dependent upon reaction temperature such that the reaction rate increases as temperature increases within the stated range. Pressure required to keep reactants at least partially in liquid phase is atmospheric up to about 500 psig depending upon temperature and reaction time. Preferably, the pressure is maintained substantially at or above the vapor pressure of the reaction mixture. After 30 minutes at 320° C., in a sealed vessel operating at the vapor pressure of its contents, a residue initially containing about 2 percent cyclohexanol yielded a reaction product containing 8 percent cyclohexanone, 6 percent cyclohexanol, and 8 percent cyclohexene. Products may be recovered as the reaction progresses or afterwards by conventional distillation methods.

EXAMPLE 2

In another series of experimental runs, one to two percent para-toluenesulfonic acid in the form of dry crystals was added to the liquid residue utilized as the starting material in Example 1, and the mixtures were shaken until the crystals were dissolved. These mixtures were placed in completely sealed stainless steel reaction bombs and heated at 150°–300° C. for 15–30 minutes. Each bomb was then rapidly cooled to room temperature. A range from 0.01 to five percent para-toluenesulfonic acid was employed with beneficial results. Temperatures of 200°–300° C. and reaction times up to 30 minutes are preferred ranges. Pressure required to keep reactants mostly in liquid phase is 100–500 psig. Preferably the pressure is maintained substantially at or above the vapor pressure of the reaction mixture. Using 2 percent para-toluenesulfonic acid at 250° C. for 20 minutes gave a yield of 15 percent cyclohexanone, 10 percent cyclohexanol and 15 percent cyclohexene. Products may be recovered as the reaction progresses or afterwards by conventional methods.

EXAMPLE 3

In another series of experimental runs, pellets of catalyst of the type normally used in hydrotreating applications (see below) and the liquid residue employed in Example 1 as starting material were added to a stirred reactor and heated to 175°–300° C. over a period of ½–2 hours and then allowed to cool. The reactor was sealed and allowed to run at the vapor pressure of its contents. The amount of catalyst used, based on liquid residue, was 10–15 percent. Catalysts, which were individually employed in the non-sulfided form, were: 10–15 percent of (a) a nickel-molybdenum catalyst (present as 3.8 percent nickel oxide and 16.8 percent molybdenum trioxide); (b) a cobalt-molybdenum catalyst (present as 3 percent cobalt oxide and 15 percent molybdenum dioxide) based on weight of liquid residue.

A range of 10–100,000 liquid residue to catalyst weight ratio is employed with beneficial results. Mixtures of the catalyst are also employed with beneficial results. Temperatures of 175°–250° C. and reaction times up to one hour are preferred ranges. Pressure may range from atmospheric up to 5000 psig.

HT-100 nickel-molybdenum catalyst, which was obtained from Harshaw Chemical Company, produced about 12 percent cyclohexene, 6 percent cyclohexanone, and 2 percent cyclohexanol in 1 hour at 225° C. HT-400 cobalt-molybdenum catalyst, which was also obtained from Harshaw Chemical Company, produced about 12 percent of cyclohexene, 8 percent cyclohexanone, and 2 percent cyclohexanol in 1 hour at 200° C. Liquid residue to catalyst weight ratio was 10 in both cases.

EXAMPLE 4

A sample of 95 percent pure 2-(1-cyclohexenyl)cyclohexanone containing no water was heated, without the addition of water or steam and without a catalyst, under its vapor pressure in a sealed vessel at 300° C. for a period of one hour. Afterwards, the vessel and contents were rapidly cooled. The resulting mixture was analyzed by gas chromatography and found to be a complex mixture containing about 12 percent cyclohexanone and 2 percent cyclohexene in addition to a number of other cleavage products amounting to about 75 percent of the mixture. Approximately 90 percent of the starting bicyclic ketone was cleaved during the process.

EXAMPLE 5

The following experiment was carried out for the purpose of comparing the hydrolytic cleavage reaction with the thermal cleavage reaction.

A sample of the high-boiling fraction from the distillation of cyclohexanone and cyclohexanol containing about 20 percent of 2-(1-cyclohexenyl)cyclohexanone and no water was placed in a pressure vessel. Another sample of the same high-boiling fraction but containing 4 percent water based on the weight of the mixture was placed in a second pressure vessel. Both vessels were then placed in an oven and allowed to operate at their respective vapor pressures at 300° C. for a period of one hour. Afterwards, the vessels were rapidly cooled and the contents of each was analyzed by gas chromatography.

The sample which contained no water was found to contain 7 percent cyclohexanone, 2 percent cyclohexanol, and 1 percent cyclohexene after conducting the cleavage. About 34 percent of the original 2-(1-cyclohexenyl)cyclohexanone was cleaved during the process. The amount of cyclohexanone corresponded to about 100 percent of the amount of bicyclic ketone cleaved thermally.

The sample which contained 4 percent water was found to contain 13 percent cyclohexanone, 2 percent cyclohexanol, and 1 percent cyclohexene. About 58 percent of the original 2-(1-cyclohexenyl)cyclohexanone was cleaved during the process. The amount of cyclohexanone corresponded to 108 percent of the amount of bicyclic ketone cleaved hyrolytically, which corresponds to theory for the hydrolytic cleavage reaction in this case.

The present invention has been specified in detail with respect to certain preferred embodiments thereof.

What is claimed is:

1. A process for thermal cleavage of unsaturated multi-cyclic ketones selected from the group consisting of 2-(1-cyclohexenyl)cyclohexanone, 2-cyclohexylidenecyclohexanone, and 2-cyclohexenylidenecyclohexanone which comprises confining the ketone in a substantially dry state, without the addition of water or steam, at a temperature from about 150° to 350° C., and under a pressure high enough to ensure that a liquid phase is present, and recovering the products therefrom.

2. The process of claim 1 wherein said multi-cyclic ketone is confined substantially at or above the vapor pressure of the multi-cyclic ketone or a reaction mixture containing said multi-cyclic ketone.

3. The process of claim 1 wherein the multi-cyclic ketone or a mixture thereof is obtained as a high-boiling fraction from the distillation of cyclohexanone and cyclohexanol.

4. The process of claim 1 which further comprises using para-toluenesulfonic acid as a catalyst.

5. The process of claim 1 which further comprises using a catalyst in the form of (a) nickel oxide/molybdenum oxide or (b) cobalt oxide/molybdenum oxide or (c) a mixture thereof, on an inert support.